United States Patent [19]

Lai

[11] Patent Number: 4,496,772

[45] Date of Patent: Jan. 29, 1985

[54] PREPARATION OF NITROALCOHOLS

[75] Inventor: John T. Lai, Broadview Heights, Ohio

[73] Assignee: The BF Goodrich Company, Akron, Ohio

[21] Appl. No.: 512,081

[22] Filed: Jul. 8, 1983

[51] Int. Cl.$^3$ .............................................. C07C 79/18
[52] U.S. Cl. ..................................... 568/704; 568/876
[58] Field of Search ................ 568/704, 740, 876, 878

[56] References Cited

U.S. PATENT DOCUMENTS 3,534,112 10/1970 Tindall ................................. 568/704
3,564,062 2/1971 Tindall ................................. 568/704
3,723,546 3/1973 Bachmen et al. .................... 568/704
4,241,226 12/1980 Adrain et al. ....................... 568/704

OTHER PUBLICATIONS

Vanderbilt et al, "Industrial and Eng. Chem.", vol. 32, (1940), TP1A54, pp. 34–38.

Primary Examiner—Werren B. Lone
Attorney, Agent, or Firm—George A. Kap; Alan A. Csontos

[57] ABSTRACT

In a process for preparing a nitroalcohol by reacting a nitroparaffin and an aldehyde in a solvent, the improvement comprising the use of 0.5 to 5 mole percent of a trialkyl phosphine, based on the nitroparaffin, which greatly reduces reaction time to 0.1 to 5 hours.

11 Claims, No Drawings

PREPARATION OF NITROALCOHOLS

BACKGROUND OF THE INVENTION

Nitroalcohols and their preparation are well known. Nitroparaffins or nitroalkanes that contain a hydrogen atom on the alpha carbon enter into condensation reactions of the aldol type to produce nitroalcohols. For instance, nitromethane condenses with propionaldehyde in alkaline solution to give 1-nitro-2-butanol. Tertiary nitroparaffins lack an alpha hydrogen and, therefore, can neither be deprotonated by alkali nor enter into condensation reactions. Preparation of nitroalcohols by condensing aldehydes with nitroparaffins dates back to at least 1900.

An article by Vanderbilt and Hass entitled "Aldehyde-Nitroparaffin Condensation" in *Industrial and Engineering Chemistry*, Vol. 32, No. 1, January 1940, pp. 34–38, provides some details relating to the preparation of nitroalcohols by condensing a nitroparaffin with an aldehyde in alkaline medium. If the nitroparaffin is secondary, there is only one alpha hydrogen atom which reacts with one mole of an aldehyde whereas if the nitroparaffin is primary, there are two alpha hydrogen atoms which react with two moles of an aldehyde. At middle of p. 35 of this article, preparation of 5-nitro-4-octanol is described whereby 2 moles of 1-nitrobutane, 100 cc of alcohol, and 4 cc of 10N sodium hydroxide solution were initially placed into a flask. Then, 2 mols of butyraldehyde were added slowly to the flask while agitating contents thereof and while maintaining reaction temperature at 30°–35°. Additional aldehyde with water was later added and the solution was allowed to stand 4 days, following which, the alkali was neutralized with hydrochloric acid and the mixture was distilled which yielded 5-nitro-4-octanol. Needless to say, the 4 days it took to prepare the nitroalcohol was excessive and unacceptable for a commercial process.

SUMMARY OF THE INVENTION

This invention relates to preparation of nitroalcohols by reacting in an organic solvent a nitroparaffin and an aldehyde in the presence of a trialkyl phosphine of the formula $R_3P$ where each R is individually selected from alkyl, aralkyl, hydroxyalkyl, cyanoalkyl, and cycloalkyl groups. The presence of a trialkyl phosphine reduces reaction time to less than about 5 hours whereas in its absence, reaction time is on the other of days.

DETAILED DESCRIPTION OF THE INVENTION

The reaction of a nitroparaffin with an aldehyde in alkaline medium has been used for nearly a century to produce nitroalcohols. The problem with this reaction has been an excessive reaction time. The IEC article noted above discloses that more than 4 days was required to react 1-nitrobutane with butyraldehyde in alkaline medium to produce 5-nitro-4-octanol. It has been discovered that the use of a trialkyl phosphine in such a reaction can unexpectedly reduce the reaction time to less than about 5 hours.

The reaction described herein essentially corresponds to the prior art reaction with the exception that it is carried out in the presence of a small amount of a trialkyl phosphine catalyst and there is no requirement to add an alkaline material to the reaction medium. The reaction between a secondary nitroparaffin and an aldehyde can be carried out in the temperature range of about room temperature to the boiling point of the solvent, preferably 30° to 50° C. The reaction can be generally represented as follows:

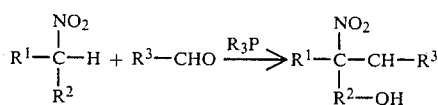

If nitroparaffin is a primary nitroparaffin, then 2 moles of an aldehyde are reacted with the same aldol reaction taking place at the second alpha hydrogen. Generally, therefore, one mole of an aldehyde will react with each alpha hydrogen on the nitroparaffin.

In the above reaction, $R^1$, $R^2$ and $R^3$ can be individually selected from hydrogen, alkyl and hydroxyalkyl groups of 1 to 12 but preferably 1 to 6 carbon atoms, and aralkyl groups of 7 to 15 but preferably 7 to 10 carbon atoms. Each of the R groups in the phosphine catalyst can be individually selected from alkyl and hydroxyalkyl groups of 1 to 12 but preferably 1 to 6 carbon atoms, aralkyl groups of 7 to 15 but preferably 7 to 10 carbon atoms, cyanoalkyl groups containing 2 to 13 but preferably 2 to 7 carbon atoms, and cycloalkyl groups containing 5 to 8 but preferably 5 to 6 carbon atoms in the ring structure and 1 to 12 but preferably 1 to 6 carbon atoms in the alkyl group.

The trialkyl phosphine catalysts can be used in amount of 0.5 to 5 mole%, preferably 1 to 3 mole%, based on nitroparaffin. Specific examples of the catalysts include tri-n-butyl phosphine, triethyl phosphine, tri-n-propyl phosphine, tri-n-octyl phosphine, tris-2-cyanoethyl phosphine, and the like.

Any suitable solvent can be used to facilitate contact between the reactants. Suitable solvents include organic solvents that can be used in amount ranging from about 10 parts to 500 parts, preferably 20 to 200 parts, per 100 parts of the reactants, all on weight basis. Specific examples of suitable solvents that can solubilize the product include isopropanol, toluene, tetrahydrofuran, methylene chloride, and the like.

Pursuant to the invention described herein, nitroalcohols, and beta-nitroalcohols specifically, can be prepared by reacting a nitroparaffin with an aldehyde, including paraformaldehyde. The reaction is conducted in presence of an organic solvent at about room temperature to the boiling point of the solvent but preferably at 30° to 50° C., and in the presence of a trialkyl phosphine catalyst. The catalyst is used at a level of 0.5 to 5 mole%, preferably at 1 to 3 mole%. The reaction is completed in 0.1 to 5 hours, preferably 0.5 to 2 hours, when the exotherm subsdies. The solvent is removed and the product can be recrystallized or distilled.

The preparation procedure involves the addition with mixing of a nitroalkane, an aldehyde, a solvent, and a small amount of the catalyst to a reaction vessel. An exotherm is generated instantly which starts to subside in about 10 minutes to 1 hour. To maintain reaction mixture at the desired temperature, external heat is applied. After about one-half hour, all of the aldehyde goes into solution and the reaction mixture becomes viscous indicating completion of the reaction.

Nitroparaffins, the reactants used in the preparation of nitroalcohols, can be made by heating alkanes in a vapor state with vapors of nitric acid at about 420° C. The nitration of propane, for instance, yields 1-nitropropane and 2-nitropropane. This mixture of nitro compounds is separated by fractional distillation into individual products which can be used as solvents or as starting materials for chemical syntheses.

The nitroparaffins or the nitroalkanes are colorless liquids of an agreeable odor. They are sparingly soluble in water but dissolve easily in most solvents. They distill without decomposition and, in contrast to the alkyl nitrates, explode with difficulty. Their boiling points are considerably higher than those of the isomeric alkyl nitrites.

The aldehydes, which are also reactants in the preparation of nitroalcohols described herein, are well known and commercially available materials. There is no limitation on the aldehyde that can be employed in preparing nitroalcohols. The reaction proceeds by condensation of an aldehyde with a nitroparaffin by extraction of an alpha hydrogen which combines with the oxygen on the aldehyde to form a hydroxyl group and the alpha carbon of the aldehyde becomes bonded to the nitroparaffin carbon which has attached thereto the nitro group.

The invention described herein will now be illustrated especially with respect to the use of a trialkyl phosphine catalyst in the preparation of beta-nitroalcohols by reacting, in a solvent, a nitroparaffin containing an alpha hydrogen and an aldehyde.

EXAMPLE 1

This example demonstrates the reaction of 2-nitropropane with paraformaldehyde in the pressence of tri-n-butyl phosphine catalyst, conducted in isopropanol solvent. The product was 2-methyl-2-nitro-1-propanol. The reaction can be depicted as follows:

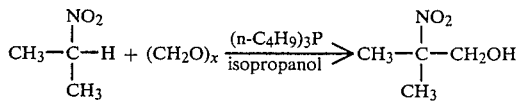

Preparation procedure involved the addition to a reaction vessel 0.1 mole of 2-nitropropane, 0.1 mole of paraformaldehyde, 40 mls of isopropanol solvent, and 0.002 mole of tri-n-butyl phosphine catalyst. Additions of the materials to the reaction vessel were made with continuous agitation. Upon addition of the catalyst, an exotherm was instantly generated and when it started to subside in about 10 minutes, external heat was applied to maintain reaction temperature at 35° to 40° C. After about one-half hour, all paraformaldehyde went into solution and the reaction mixture became viscous, indicating completion of the reaction. The product solidified on standing after removal of solvent. Total reaction time was about ¾ of an hour.

EXAMPLE 2

Following the procedure set out in Example 1, above, 0.1 mole of nitroethane was reacted with 0.2 mole of paraformaldehyde in isopropanol solvent in the presence of t-n-butyl phosphine catalyst. The product recovered was 2-methyl-2-nitro-1,3-propanol. Total reaction time was about ¾ of an hour.

EXAMPLE 3

Following the procedure set forth in Example 1, above, 0.1 mole of 1-nitropropane was reacted with 0.2 mole of paraformaldehyde in toluene solvent using t-n-butyl phosphine as the catalyst. The product was 2-nitro-1-butanol. Total reaction time was about 1 hour.

EXAMPLE 4

Following procedure of Example 1, above, 0.1 mole of nitroethane was reacted with 0.2 mole of n-butyraldehyde in tetrahydrofuran solvent using tris-(2-cyanoethyl)phosphine as the catalyst. Recovered product was 2-nitro-3-hexanol. Total reaction time was about 2 hours.

I claim:
1. In a process for preparing a nitroalcohol by reacting a nitroparaffin with an aldehyde, the improvement comprising the step of conducting the reaction in the presence of trialkyl phosphine catalyst.

2. Process of claim 1 wherein said trialkyl phosphine can be represented as $R_3P$ where each of the three R groups is individually selected from alkyl and hydroxyalkyl groups of 1 to 6 carbon atoms, aralkyl groups of 7 to 10 carbon atoms, cyanoalkyl groups of 2 to 7 carbon atoms, and cycloalkyl groups of 5 to 6 carbon atoms in the ring structure and 1 to 6 carbon atoms in the alkyl group.

3. Process of claim 1 wherein said reaction is carried out in a solvent selected from isopropanol, toluene, tetrahydrofuran, methylene chloride, and 2-propanol.

4. Process of claim 1 wherein amount of said catalyst is in the range of about 0.5 to 5 mole percent, based on said nitroparaffin.

5. Process of claim 3 wherein amount of said catalyst is in the range of about 1 to 3 mole percent, based on said nitroparaffin, and said reaction is carried out at a temperature in the range of room temperature to the boiling point of the solvent, at standard atmospheric conditions.

6. Process of claim 5 wherein amount of said aldehyde is approximately on a molar equivalent basis based on the equivalents of said nitroparaffin as related to the number of alpha hydrogens on said nitroparaffin.

7. Process of claim 6 wherein said nitroparaffin and said aldehyde can be represented as follows:

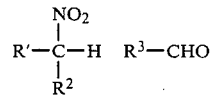

where each $R^1$ and $R^2$ group is selected from hydrogen, alkyl and hydroxyalkyl groups of 1 to 12 carbon atoms, and aralkyl groups of 7 to 15 carbon atoms; and $R^3$ is selected from hydrogen, alkyl groups of 1 to 12 carbon atoms, and aralkyl groups of 7 to 15 carbon atoms, and multiples thereof.

8. Process of claim 7 wherein each $R^1$ and $R^2$ group is selected from hydrogen, alkyl and hydroxyalkyl groups of 1 to 6 carbon atoms, aralkyl groups of 7 to 10 carbon atoms; and $R^3$ is selected from hydrogen and alkyl groups of 1 to 6 carbon atoms.

9. Process of claim 4 for the preparation of beta-nitroalcohols wherein said reaction is carried out by mixing said nitroparaffin, said aldehyde, and said catalyst in said solvent, maintaining temperature in the range of about 30° to 50° C. after initial exotherm subsides, and continuing said reaction for about 0.1 to 5 hours until the reaction mixture becomes viscous, indicating completion of the reaction.

10. Process of claim 9 wherein the reaction time is 0.5 to 2 hours, said reacting step is conducted at about 30° to 50° C., and said process includes the step of recovering said nitroalcohol.

11. Process of claim 9 wherein said nitroparaffin is selected from 2-nitropropane; said aldehyde is selected from paraformaldehyde; said catalyst is selected from tri-n-butylphosphine; and said solvent is selected from 2-propanol.

* * * * *